(12) United States Patent
Cole

(10) Patent No.: US 6,479,726 B1
(45) Date of Patent: Nov. 12, 2002

(54) SANITARY DEVICE FOR URINARY INCONTINENT MALES

(76) Inventor: Walter E. Cole, 14621 Laurel Oak Ct., Baton Rouge, LA (US) 70810

(*) Notice: Subject to any disclaimer, the term of this patent is extended or adjusted under 35 U.S.C. 154(b) by 204 days.

(21) Appl. No.: 09/648,434

(22) Filed: Aug. 25, 2000

(51) Int. Cl.[7] .......................... A61F 13/15; A61F 13/12
(52) U.S. Cl. .................... 604/358; 604/326; 604/327; 604/348-355; 604/317-325; 604/328-347; 604/349; 604/350; 604/351; 604/352; 604/353
(58) Field of Search .................. 604/326, 327, 604/348–354, 355, 325, 328–347, 349, 350, 351, 352, 353, 356–402

(56) References Cited

U.S. PATENT DOCUMENTS

| | | | | |
|---|---|---|---|---|
| 3,958,574 A | * | 5/1976 | Rohr | 128/295 |
| 4,064,880 A | * | 12/1977 | Logan | 128/294 |
| 4,576,599 A | * | 3/1986 | Lipner | 604/390 |
| 4,863,448 A | * | 9/1989 | Berg | 604/349 |
| 4,971,074 A | * | 11/1990 | Hrubetz | 128/885 |
| 5,074,853 A | * | 12/1991 | Bryant | 604/349 |
| 5,322,071 A | * | 6/1994 | Ambrose | 128/849 |
| 5,643,235 A | * | 7/1997 | Figuerido | 604/352 |
| 5,695,485 A | * | 12/1997 | Duperret et al. | 604/349 |
| 5,702,381 A | * | 12/1997 | Cottenden | 604/385.1 |
| 5,746,222 A | * | 5/1998 | Simon et al. | 128/885 |
| 6,338,729 B1 | * | 1/2002 | Wada et al. | 604/385.09 |

FOREIGN PATENT DOCUMENTS

| | | | |
|---|---|---|---|
| WO | WO 86/05387 | * | 9/1986 |
| WO | WO 87/07136 | * | 12/1987 |
| WO | WO 89/00037 | * | 1/1989 |
| WO | WO 89/11839 | * | 12/1989 |

* cited by examiner

Primary Examiner—Jeanette Chapman
(74) Attorney, Agent, or Firm—David L. Ray

(57) ABSTRACT

A sanitary device which may be applied and connected to the penis of a man suffering from urinary incontinence to contain urine emitted involuntarily, the sanitary device including an absorbent sheath for wrapping around and enclosing the penis, the sheath being made from a continuous piece of water impermeable material lined with a layer of absorbent material, the sheath having a generally rectangular front face and a substantially identical generally rectangular rear face, the sheath having an open bottom edge and an open side edge, the open bottom edge being adjacent to the open side edge, the sheath having a closed side edge and a closed top edge which connect the front face to the rear face, and the closed side edge being adjacent to the closed top edge. Preferably, the rear face has adhesive tape thereon for fastening the rear face to the front face to secure the sanitary device to the penis.

18 Claims, 2 Drawing Sheets

SANITARY DEVICE FOR URINARY INCONTINENT MALES

BACKGROUND OF THE INVENTION

1. Field of the Invention

The present invention relates to devices used to contain and absorb urine. In particularly, the present invention is related to devices for use by urinary incontinent males to contain involuntary urine emissions.

2. Description of the Related Art

Various devices and implements are known in the art for absorbing and containing urine flow. See for example U.S. Pat. Nos.: 3,958,574; 4,576,599; 4,863,448; 4,971,074; 5,074,853; 5,643,235; 5,695,485; 5,702,381; and 5,746,222 and Foreign Patents: PCT WO 86/05387; PCT WO 87/07136; PCT WO 89/00037; and PCT WO 89/11839.

Urinary incontinence is a problem for many men who are elderly, or have, or are recovering from, prostate cancer. The only commonly available device for men suffering from urinary incontinence are diapers or absorbent pads which cover both the penis and the rectum. Such diapers are used primarily by men who are totally incontinent and who cannot control any of their excretory functions. Full-size diapers are expensive and uncomfortable for persons suffering only from urinary incontinence.

SUMMARY OF THE INVENTION

It is thus an object of the invention to provide a sanitary device to absorb and contain urine which can be worn by a man suffering from urinary incontinence.

Another object of the present invention is to provide a sanitary device for men suffering from urinary incontinence which is disposable and low in cost.

It is another object of the invention to provide a sanitary device for men suffering from urinary incontinence which may be quickly and easily applied and connected to the penis of the user.

In accordance with the present invention there is provided a sanitary device which may be applied and connected to the penis of a man suffering from urinary incontinence to contain urine emitted involuntarily, the sanitary device including an absorbent sheath for wrapping around and enclosing the penis, the sheath being made from a continuous piece of water impermeable material lined with a layer of absorbent material, the sheath having a generally rectangular front face and a substantially identical generally rectangular rear face, the sheath having an open bottom edge and an open side edge, the open bottom edge being adjacent to the open side edge, the sheath having a closed side edge and a closed top edge which connect the front face to the rear face, the closed side edge being adjacent to the closed top edge. Preferably, the rear face has adhesive tape thereon for fastening the front face to the rear face.

The present invention has the advantage of being low in cost.

The present invention has the advantage of being easily connected to the penis of the user.

The present invention has the further advantage of being low in cost and disposable.

DESCRIPTION OF THE PREFERRED EMBODIMENTS

Figure 5:
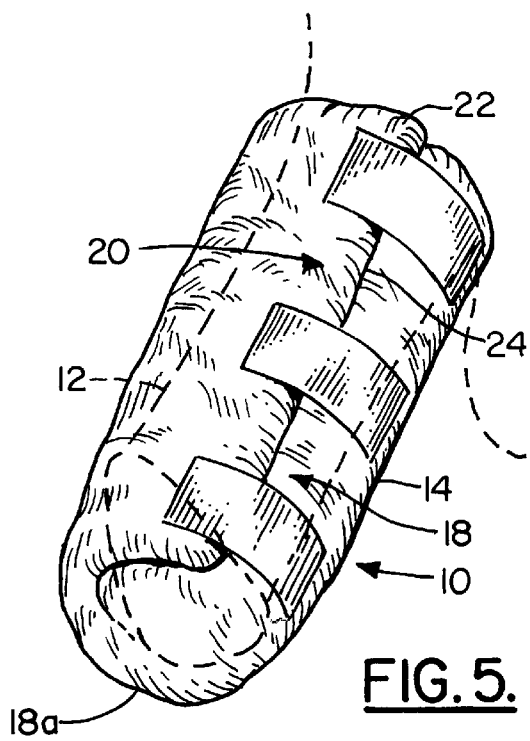
FIG. 5 is a perspective view of the sanitary device of the invention connected to the penis of the user shown in phantom lines.

Referring now to the drawings, and in particular to FIG. 5, the sanitary device of the present invention is generally indicated by the numeral 10. Sanitary device 10 is an absorbent, urine-containing sheath for wrapping around and enclosing the penis of the user indicated by the numeral 12 in FIG. 5.

Sanitary device 10 is constructed from a continuous piece of material having an outer layer 14 of water-impermeable or hydrophobic material which prevents any urine emitted from penis 12 from escaping from the interior of sanitary device 10 when sanitary device 10 is wrapped around penis 12 as shown in FIG. 5. Connected to water impermeable layer 14 of sanitary device 10 is a layer of liquid absorbent material 16 which absorbs urine emitted from penis 12. Such two-layered material is well known in the art and is commonly used to construct commercially available sanitary napkins, disposable diapers, and the like.

Figure 1:
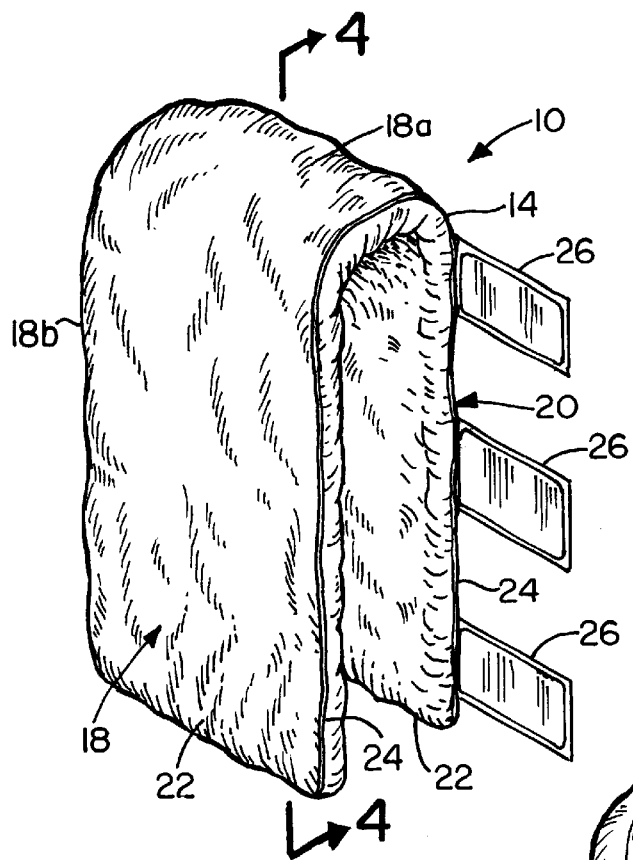
FIG. 1 is a perspective view of the sanitary device of the invention.
Figure 2:
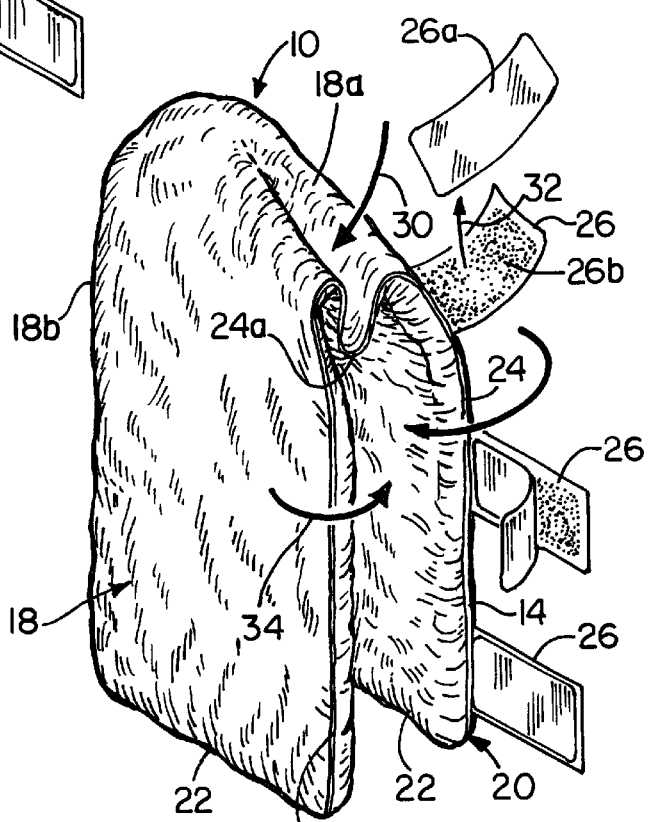
FIG. 2 is a perspective view: of the sanitary device of the invention being folded about the penis of the user.
Figure 4:
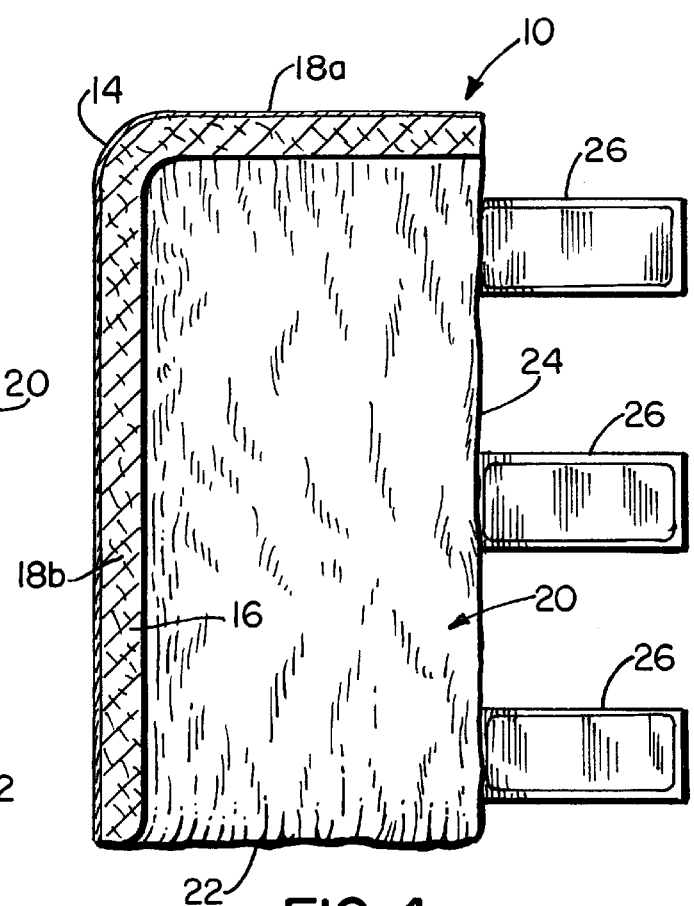
FIG. 4 is a cross-sectional view taken along lines FIG. 4—4 of FIG. 1.

As shown in FIGS. 1, 2, and 4, in the free-standing or un-wrapped position, sanitary device 10 is generally rectangular in shape and shaped from a continuous piece of two-layer material as stated above. Sanitary device 10 has a generally rectangular front face 18 and a substantially identical generally rectangular rear face 20 connected together at topedge 18a and at side edge 18b.

Sanitary device 10 has an open, U-shaped bottom edge 22 which lies substantially in a plane as shown in FIGS. 1–5, and an open, U-shaped side edge 24 which lies substantially in a plane in the view shown in FIGS. 1, 2, and 4. The plane containing bottom edge 22 is substantially perpendicular-to the plane containing open, U-shaped side edge 24 when side edge 24 is in the position shown in FIGS. 1, 2, and 4.

Figure 3:
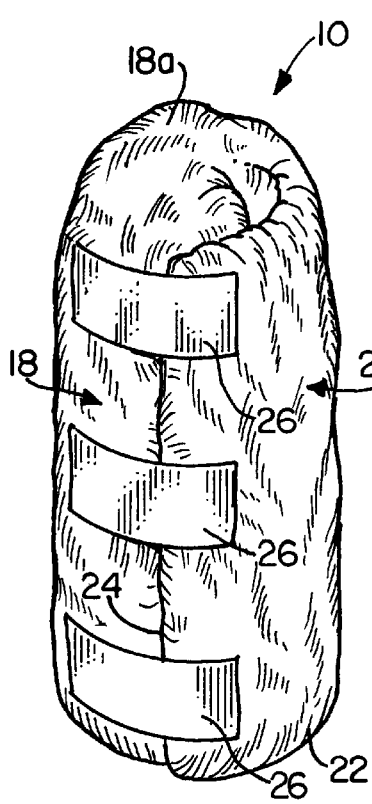
FIG. 3 is a perspective view of the sanitary device of the invention wrapped about the penis of the user and secured in place by tape.

Preferably, rear face 20 has a conventional adhesive tape 26 connected thereto. Adhesive tape 26 is well known in the art and will adhere to the front face 18 when sanitary device 10 is wrapped about the penis 12 of the wearer as shown in FIGS. 3 and 5. Preferably tape 26 has a peelable strip 26a thereon which can be removed by the user as shown by arrow 32 in FIG. 2 to expose an adhesive material 26b therebeneath, as is well known in the art. If desired, adhesive tape 26 could be omitted from rear face 20 and replaced with commonly available adhesive tape dispensed from a conventional roll of adhesive tape.

To utilize the sanitary device 10 of the invention to contain urine involuntary emitted from the penis 12 of a urinary incontinent male, the sanitary device 10 is wrapped about penis 12, and rear face 20 is fastened to front face 18 with adhesive tape 26 as shown in FIGS. 2 and 5.

As shown in FIG. 5, to facilitate a smooth wrap of sanitary device 10 about the penis 12 of the user, the shaft of penis 12 is placed inside front face 18 and rear face 20 adjacent to closed side edge 18b with the distal end of penis 12 adjacent to top edge 18a and the base of penis 12 adjacent to bottom edge 22. The length of side edge 18b and the length side edge 24 can be selected as desired to accommodate different lengths of penis 12. The length of bottom edge 22 and the length of top edge 18a can be selected as desired to accommodate different diameters of penis 12.

As shown in FIG. 2, the top center portion of top edge 18a and side edge 24 is preferably forced downward as indicated by arrow 30 to form a fold 24a, peelable strip 26a is removed from adhesive tape 26 as shown by arrow 32 to expose adhesive material 26b, the open edge 24 of front face 18 is wrapped around the shaft of the penis 12 and fold 24a as indicated by the arrow 34, the open edge 24 of rear face 20 containing adhesive strips 26 is wrapped over the surface of front face 18, and adhesive tape 26 is connected to the surface of front face 18 to securely fasten sanitary device 10 around penis 12.

After use, the sanitary device 10 is easily removed from the penis 12 by pulling the sanitary device 10 directly away from the distal end of the penis 12, or by tearing the tape 26 from the surface of front face 18.

Although the preferred embodiments of the invention have been described in detail above, it should be understood that the invention is in no sense limited thereby, and its scope is to be determined by that of the following claims:

What is claimed is:

1. A sanitary device which may be applied and connected to the penis of a man suffering from urinary incontinence to contain urine emitted involuntarily, the sanitary device comprising an absorbent sheath for wrapping around and enclosing said penis, said sheath being made from a continuous piece of water impermeable material lined with a layer of absorbent material, said sheath having a generally rectangular front face and a substantially identical generally rectangular rear face, said sheath having an open bottom edge and an open side edge, said open bottom edge being adjacent to said open side edge, said sheath having a closed side edge and a closed top edge which connect said front face to said rear face, said closed side edge being adjacent to said closed top edge.

2. The sanitary device of claim 1 wherein said open bottom edge is U-shaped.

3. The sanitary device of claim 2 wherein said open side edge is U-shaped.

4. The sanitary device of claim 3 wherein said open U-shaped bottom edge lies substantially in a plane and said open, U-shaped side edge lies substantially in a plane.

5. The sanitary device of claim 4 wherein said plane containing said open, U-shaped bottom edge is substantially perpendicular to said plane containing said open, U-shaped side edge.

6. The sanitary device of claim 5 wherein said rear face has adhesive tape connected thereto which will adhere to the top surface of said front face when said rear face is wrapped about said penis and over said front face.

7. The sanitary device of claim 6 wherein said closed top edge of said sheath is foldable downward when said penis is inserted into said sheath adjacent to said closed side edge to form a fold.

8. The sanitary device of claim 7 wherein said front face is wrappable over said fold and the shaft of said penis.

9. The sanitary device of claim 8 wherein said rear face is wrappable over said front face.

10. A sanitary device which may be applied and connected to the penis of a man suffering from urinary incontinence to contain urine emitted involuntarily, the sanitary device comprising an absorbent sheath means for wrapping around and enclosing said penis, said sheath means being made from a continuous piece of water impermeable material lined with a layer of absorbent material, said sheath means having a generally rectangular front face and a substantially identical generally rectangular rear face, said sheath having an open bottom edge and an open side edge, said open bottom edge being adjacent to said open side edge, said sheath having a closed side edge and a closed top edge which connect said front face to said rear face, said closed side edge being adjacent to said closed top edge.

11. The sanitary device of claim 10 wherein said open bottom edge is U-shaped.

12. The sanitary device of claim 11 wherein said open side edge is U-shaped.

13. The sanitary device of claim 12 wherein said open U-shaped bottom edge lies substantially in a plane and said open, U-shaped side edge lies substantially in a plane.

14. The sanitary device of claim 13 wherein said plane containing said open, U-shaped bottom edge is substantially perpendicular to said plane containing said open, U-shaped side edge.

15. The sanitary device of claim 14 wherein said rear face has adhesive tape connected thereto which will adhere to the top surface of said front face when said rear face is wrapped about said penis and over said front face.

16. The sanitary device of claim 15 wherein said closed top edge of said sheath is foldable downward when said penis is inserted into said sheath adjacent to said closed side edge to form a fold.

17. The sanitary device of claim 16 wherein said front face is wrappable over said fold and the shaft of said penis.

18. The sanitary device of claim 17 wherein said rear face is wrappable over said front face.

* * * * *